United States Patent [19]
Phan

[11] Patent Number: 5,939,648
[45] Date of Patent: Aug. 17, 1999

[54] SYSTEM AND METHOD OF INTRODUCING A SAMPLE FOR ANALYTICAL ATOMIC SPECTROMETRY ALLOWING CONCOMITANT ANALYSIS OF MERCURY

[75] Inventor: Canh-Vang Phan, Verrieres-Le-Buisson, France

[73] Assignee: Instruments S.A., Paris, France

[21] Appl. No.: 08/770,774

[22] Filed: Dec. 20, 1996

[30] Foreign Application Priority Data

Dec. 22, 1995 [FR] France .................................. 95-15430

[51] Int. Cl.⁶ ........................................................ G01N 1/28
[52] U.S. Cl. ............................... 73/864.81; 73/863.12; 356/36; 356/311; 250/288
[58] Field of Search ........................... 73/864.81, 863.23, 73/863.21, 23.2, 23.41, 863.12, 863.11; 250/288 R, 288 A; 356/36, 311

[56] References Cited

U.S. PATENT DOCUMENTS

| | | | |
|---|---|---|---|
| 4,361,401 | 11/1982 | Smith, Jr. et al. | 356/36 |
| 4,559,808 | 12/1985 | Sturman | 73/23 |
| 4,667,100 | 5/1987 | Lagna | 250/288 |
| 5,018,855 | 5/1991 | Davison et al. | 73/864.21 |
| 5,237,385 | 8/1993 | Pfeil et al. | 73/864.81 |
| 5,259,254 | 11/1993 | Zhu et al. | 73/864.81 |

FOREIGN PATENT DOCUMENTS

| | | |
|---|---|---|
| 1-170840 | 5/1989 | Japan . |
| 1-170841 | 7/1989 | Japan . |

OTHER PUBLICATIONS

Patent Abstracts of Japan, 13 (443), (P–491), Oct. 10, 1989.
Patent Abstracts of Japan, 10 (298), (P–505), Oct. 10, 1986.

*Primary Examiner*—Hezron Williams
*Assistant Examiner*—Nashmiya Fayyaz
*Attorney, Agent, or Firm*—Millen, White, Zelano & Branigan, P.C.

[57] ABSTRACT

A system for introducing a liquid sample (1) for analytical atomic spectrometry includes a nebulizer (20) and separator (27) at the exit (23) of the nebulizer. The system also includes at least one drain (30) fitted with evacuator (16, 17) for evacuating residual liquid (8) in a constricted and controlled flow, and reagent supplier (12, 13) for supplying drain (30) with a reagent (2) to generate hydride.

24 Claims, 1 Drawing Sheet

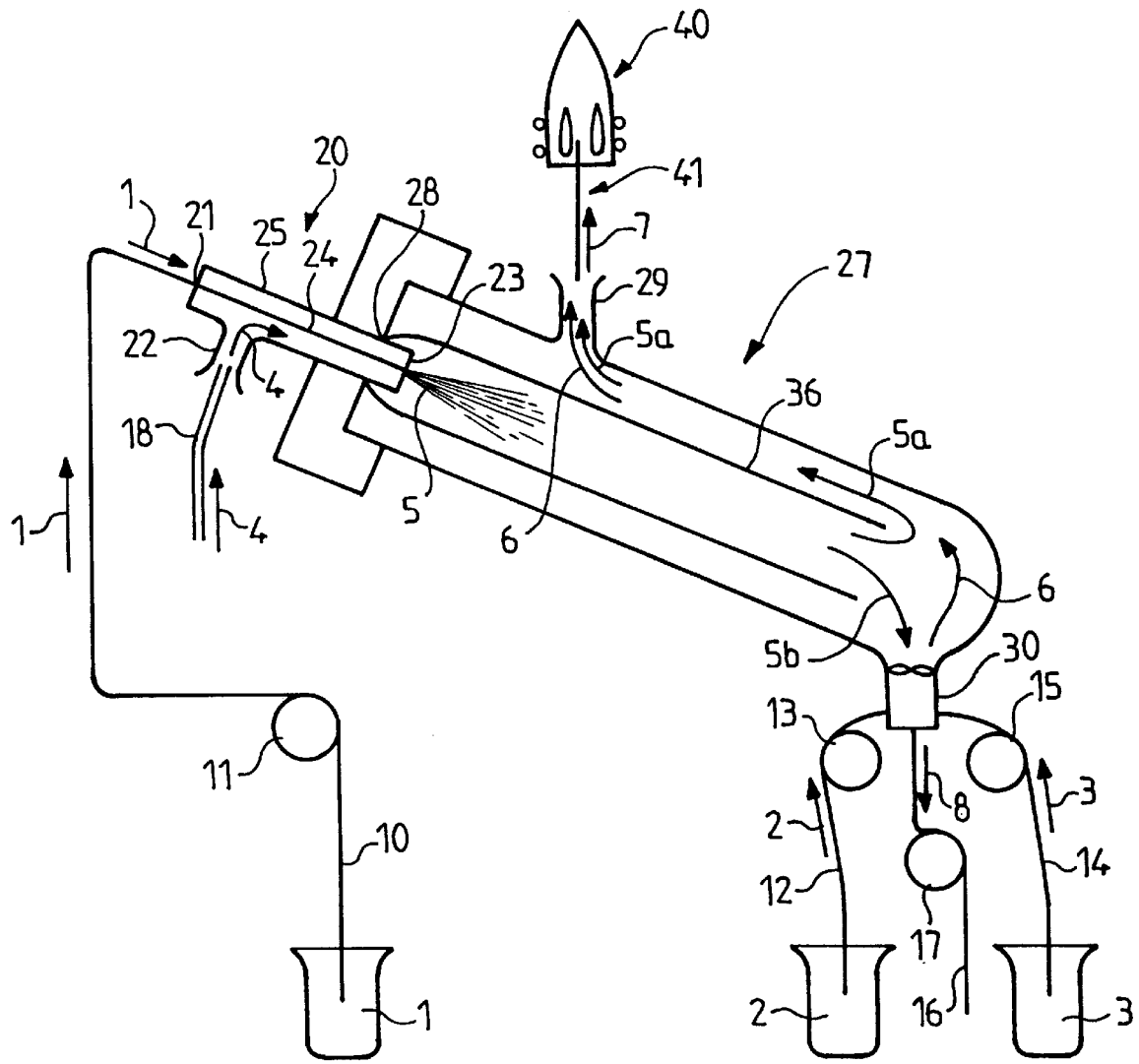
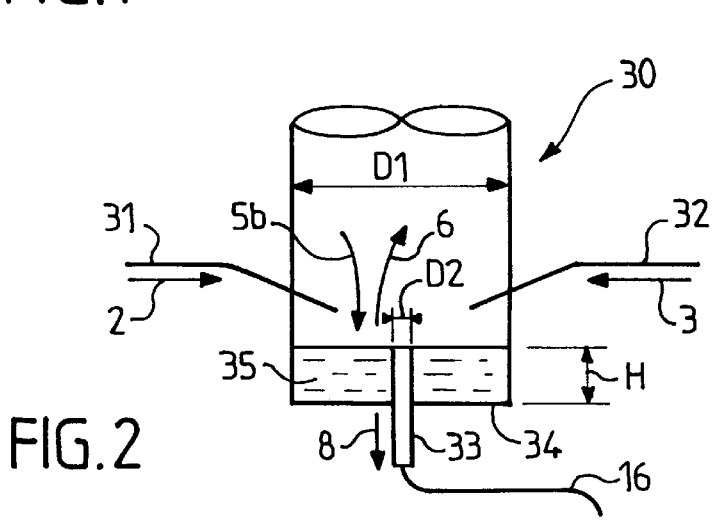
FIG.1
FIG.2

SYSTEM AND METHOD OF INTRODUCING A SAMPLE FOR ANALYTICAL ATOMIC SPECTROMETRY ALLOWING CONCOMITANT ANALYSIS OF MERCURY

BACKGROUND OF THE INVENTION

The present invention relates to a system and method of introducing a sample for analytical atomic spectrometry. It finds application in particular in the analysis of products in liquid form, in solution, or in suspension in a liquid, such as stones, earth and sediment, drinking waters, residual waters, oils, foods and biological and metallurgical samples.

Analytical atomic spectrometry is a powerful method of analysis. It consists of introducing a liquid sample into means of treatment coupled with means of spectrometric analysis to produce spectra representing the bodies contained in the sample. Four forms of analytical atomic spectrometry are known: Atomic Absorption Spectrometry or AAS; Atomic Emission Spectrometry or AES; atomic fluorescence, and Mass Spectrometry or MS.

Traditionally, atomic absorption consists of introducing the solution into a flame at very high temperature, conventionally in the region of 2000 to 3000° C., lit by a lamp corresponding to the bodies to be analysed. This lamp is, for example, a hollow cathode lamp and usually allows the analysis of one to three elements, such as, for example, mercury or chromium. The light emitted by the lamp after crossing through the flame is subjected to spectrometric means which show absorption due to the solution ionised in the flame.

One of the most widely used atomic emission techniques is Inductively Coupled Plasma atomic emission spectrometry—ICP-AES.

Similarly, a technique frequently used for mass spectrometry is the ICP technique, or ICP-MS.

For all analytical atomic spectrometry techniques, the means of introducing the sample is of determinant importance for the success of analysis. But, it is often necessary to obtain a very low concentration detection limit. In particular, analysis of toxic elements in water requires very high sensitivity in order to reach promulgated, authorised limits.

One of the most effective means of introducing the sample consists of previous nebulisation with a nebuliser. With nebulisation it is possible to spray the sample into fine droplets so that the energy used by the analytical atomic spectrometry means, aside from that required for ionisation, is substantially reduced.

The nebuliser that is conventionally used is a pneumatic nebuliser, comprising an inlet for the liquid to be analysed, an inlet for a vector gas, and an expelling outlet for fine droplets in suspension in the vector gas derived from spraying of the liquid. The pneumatic nebuliser usually leads to a spray chamber where the largest droplets can be removed which will improve the stability of the spectrum emission. The spray chamber comprises an aerosol outlet directed towards the analytical atomic spectrum spectrometry means, and a drain allowing the evacuation in liquid form of the large droplets not included in the aerosol. In these pneumatic nebulisers, only a small part of the drops containing the bodies to be analysed is effectively directed towards the spectrometry means representing approximately 5% of the solution introduced into the nebuliser. Examples of pneumatic nebulisers and spray chambers can be found in the document published by Barry L. Sharp <<Pneumatic nebulisers and spray chambers for inductively coupled plasma spectrometry—A Review>>, Journal of Analytical Atomic Spectrometry, vol.3, 1988, pp.613–652.

In order to increase the sensitivity of analytical atomic spectrometry systems, ultrasound nebulisers have been suggested. The latter spray the solutions to be analysed in generally more efficient manner than pneumatic nebulisers allowing a gain of approximately a factor of 10 in the signal to noise ratio. Despite this gain, the detection limits for a certain number of elements, in particular mercury, do not reach required limits.

Another technique for introducing samples is the generation of hydrides. This consists of mixing the solution to be analysed with a reagent chosen to produce volatile hydrides formed from certain elements contained in the solution. The hydrides thus generated are introduced directly in gas form into the analytic atomic spectrometry means. This technique, which operates for certain specific elements, leads to a higher level of performance than that of ultrasound nebulisers and allows very low detection limits to be reached. However, it requires complex handling operations and raise stability problems of the hydrides obtained.

Systems have been suggested which use both hydride generation and nebulisation. Jacques Borgnon and Jean-Louis Cadet, in <<Analyse des éléments Hg, Se, As, Sn, Sb et Bi en vapeur froide et hydrures par spectrométrie d'emission ICP>>, Analusis, Vol. 16, num.4, 1988, pp. 77–80, suggest a system comprising a multi-pathway peristaltic pump leading a solution to be analysed and an alkaline solution of borohydride towards a reactor intended to mix the latter, a mixing duct leaving the reactor and passing through a coil designed to increase the reaction time, and a bubbling-decanting jar at the end of this duct for gas-liquid separation and removal of the latter. The gas leaving the jar is led to a plasma torch via vector argon. The presence of the borohydride solution achieves a sensitivity gain of between 50 and 100 in comparison with direct spraying. However, the nebulisation of hydrides raises stability-related problems.

The abstract of Japanese Patent JP-01170840 describes a nebulisation system comprising a spray chamber and a nebuliser introduced into the chamber, and a drain tube extended by a U-shaped tube. A reducing agent is introduced into the drain tube in such manner as to generate hydrides.

This system makes control of reaction volume difficult, causes loss of generated gas and leads to pollution between successively introduced samples.

SUMMARY OF THE INVENTION

The objective of the present invention is a system for introducing a solution which allows the concomitant introduction into a plasma, without reciprocal disturbance, of an aerosol generated by a pneumatic nebuliser and of volatile hydrides generated by a hydride generator.

The object of the invention is more generally a system of introducing a solution, to be measured by analytical atomic spectrometry, that is both very sensitive and stable.

The purpose of this invention is such a system which is fully pollution-free between successively introduced samples.

The invention is particularly intended for said introduction system applicable to the precise measurement of Mercury (Hg) but also of the elements As, Bi, Ge, Pb, Sb, Se, Sn and Te.

The invention also relates to such a system that is simple to be performed and used.

The purpose of the invention is therefore to remedy the above-mentioned disadvantages of existing systems.

An additional objective of the invention is a method for introducing a liquid sample, to be analysed by analytical atomic spectrometry, offering the same advantages as those described above for the system.

For this purpose the object of the invention is a system of introducing a liquid sample containing at least one body to be analysed by analytical atomic spectrometry. This system comprises:

- at least one nebuliser able to spray the liquid sample into fine droplets, having at least one liquid inlet intended to receive the liquid sample, at least one gas inlet intended to receive a vector gas and at least one outlet intended to expel the drops in suspension in the vector gas,
- means of supplying the nebuliser with the liquid sample, connected to the liquid inlet of the nebuliser,
- means of supplying the nebuliser with vector gas connected to the gas inlet of the nebuliser,
- means of separating bodies into a first part and a second part placed at the exit of the nebuliser comprising at least one aerosol outlet intended to expel the first part of the bodies to be analysed in aerosol form towards means of analytical atomic spectrometry.
- at least one drain intended to evacuate a residual liquid, such drain receiving the second part of the bodies to be analysed in liquid form and serving to generate hydrides produced by the second part of the bodies carried by the vector gas,
- means of supplying the drain with at least one reagent intended to react with the bodies to form the hydrides.

According to the invention, the drain is plugged up and fitted with means of evacuating the residual liquid.

The sample introducing system of the invention differs from existing systems in that it combines nebulisation and hydride generation in an original manner.

In particular, it sets itself aside from existing systems using both a hydride generator and a nebuliser particularly in that the drain is plugged up and is fitted with means of evacuating residual liquid.

It may be used for production of an aerosol, for the generation of hydrides or for both at the same time, without the change from one type of use to another implying any assembly or dismounting of any unit whatsoever.

Aerosol production and hydride generation are simultaneous and therefore permit spectrometric analysis of hydride elements at the same time without any change in sample introduction.

With this system of sample introduction it is possible to obtain very high sensitivity and a very low detection limit for elements able to form hydrides. Also, it solves stability problems raised by other existing systems using hydride generation. It is also easy to use and may be set up using a conventional pneumatic stabiliser and spray chamber.

With the system of the invention it is also possible to control reaction volume, to use all the hydrides generated for analysis, to fully overcome pollution between successively introduced samples and to adapt reaction volume to a strict minimum value that is necessary to ensure complete reaction.

The sample introduction system advantageously comprises means of supplying the drain with acid.

Therefore, the sample and acid are mixed in the drain itself, after nebulisation, unlike conventional hydride generation systems in which the sample is mixed with the acid before being combined with the reagent.

Preferably, the means of supply are able to provide continuous, constant flows during analysis of the bodies.

This advantageous characteristic concerns both the means of supplying the nebuliser with liquid sample, and the means of supplying the drain with reagents, and possibly with acid and liquid sample.

In this manner, a continuous reaction is produced in contrast with Batch Type processing, such continuity allowing use to be made of the available flow of solution to be analysed without it being necessary to store an additional quantity of sample for these measurements. Also, flow constancy prevents instability formation.

The system of the invention can be used for the analysis of bodies examined by atomic spectrometry in general. It is well adapted to emission spectrometry (AES), preferably of ICP type.

The system of the invention therefore leads the aerosol and hydrides formed in the spray chamber towards a plasma torch. It constitutes a particular case of HG-ICP-AES type systems (Hydride Generation—Inductively Coupled Plasma—Atomic Emission Spectrometry) whose excellent signal to noise ratio is known in comparison with simple pneumatic nebulisation.

The nebuliser is advantageously a pneumatic nebuliser.

The embodiment obtained is therefore particularly simple.

The invention also relates to a method of introducing a liquid sample containing at least one body to be analysed by analytical atomic spectrometry, in which:

- a liquid sample and a vector gas are introduced into a nebuliser,
- the liquid sample is sprayed into fine droplets by the nebuliser and the droplets suspended in the gas are led into means of separating the bodies into a first and second part,
- the first part of the bodies to be analysed is expelled in aerosol form towards analytical atomic spectrometry means,
- the bodies contained in the aerosol are analysed by analytical atomic spectrometry.

Also, with this method:

- the second part of the bodies to be analysed is received in liquid form in a drain,
- at least one reagent is introduced into the drain intended to react with the bodies to form hydrides,
- hydrides are generated in the drain and the hydrides are carried by the vector gas towards spectrometry means, and
- residual liquid is evacuated through the drain.

According to the invention, as the drain is plugged up, the residual liquid is evacuated by drain evacuation means.

The hydrides, in gas form, are therefore led concomitantly with the aerosol towards the spectrometry means.

The flow of introduction of the liquid sample into the nebuliser and of the reagent into the hydride generator is preferably continuous and constant during analysis.

In a preferred embodiment of the method of the invention, a constant level of liquid is maintained in the drain.

Maintaining a constant level of liquid in the drain carries much importance for stability of measurements. As flows are continuous and constant, evacuation must be similarly conducted at a suitable flow rate.

Advantageously, at least one acid is introduced into the hydride generator.

The bodies are advantageously chosen from the group made up of the elements As, Bi, Ge, Hg, Pb, Sb, Se, Sn and Te.

These elements, among others, are known as being able to produce hydrides in the presence of appropriate reagents and acids.

Other characteristics and advantages of the invention shall be demonstrated on reading a particular embodiment described below with reference to the drawings. In these drawings:

FIG. 1 represents a diagrammatic section of a nebulising system of the invention.

FIG. 2 shows a detailed view of the drain for the system shown in FIG. 1.

A system for analytical atomic spectrometry, such as represented in FIG. 1, is intended for the analysis of a solution of a sample 1. This system of analysis comprises means of analytical atomic spectrometry comprising in particular, in addition to conventional spectrometry instruments, a plasma torch 40 with which ICP-AES measurements can be made. As a purely illustrative example, plasma torch 40 comprises a coil subjected to magnetic induction by a high frequency generator whose power is in the region of 1 to 2 kW. This coil ensures ionisation of the gas to create a plasma. Means of argon supply are associated with the coil. Any other method of use or embodiment of plasma torch 40 is valid within the limits of the invention.

The analysis system comprises means of introducing plasma 1 into plasma torch 40 in the form of a nebulisation device. The latter comprises in particular a concentric nebuliser 20 and a Scott chamber 27. The concentric nebuliser 20 is a pneumatic nebuliser comprising an inner duct 24 intended for the circulation of sample 1 in liquid form, and an outer duct 25 surrounding inner duct 24 provided for the circulation of a vector gas 4. Nebuliser 20 has a liquid inlet 21 opening onto inner duct 24, and a gas inlet 22 through which vector gas 4 can be introduced into outer duct 25. The purpose of nebuliser 20 is to provide, through an expelling outlet 23 to which lead inner 24 and outer 25 ducts, fine droplets 5 sprayed into vector gas 4 in the form of an aerosol.

The system of nebulisation comprises means of supplying nebuliser 20 with sample 1, such as a peristaltic pump 11 acting on a tube 10 connected to liquid inlet 21, and means of supplying nebuliser 20 with vector gas 4, comprising in particular a duct 18 leading to gas inlet 22.

Nebuliser 20 opens into a tube 36 which is approximately cylindrical and placed in Scott chamber 27 through an opening 28. Tube 36 is intended to contribute towards separation of droplets 5 sprayed into a first part 5a in aerosol form carried by vector gas 4, and into a second part 5b in liquid form. Scott chamber 27 has walls made up of an inert matter, glass for example, or a plastic material. It comprises an aerosol outlet 29 opening onto an injector 41 leading to plasma torch 40, for exiting of the first part of droplets 5a in aerosol form. It also comprises an approximately round cylindrical drain 30, provided for evacuating the second part of droplets 5b in liquid form. The walls of drain 30 are preferably made of inert matter such as glass or a plastic material. Pumping means, in the form of an evacuation tube 16 connected to drain 30 by an evacuation capillary 33 and a peristaltic pump 17 acting on tube 16 are provided to evacuate residual liquid 8 formed in drain 30.

According to one characteristic of the invention, drain 30 is fitted with supply means intended to introduce one or several reagents 2. Reagent 2 is able to form hydrides with at least one body contained in sample 1. The means of reagent 2 supply comprise a tube 12 on which operates a peristaltic pump 13, leading into drain 30 through a needle 31.

A further distinctive feature of the sample introduction system of the invention is that it comprises means of supplying drain 30 with one or more acids 3. Acid 3 is intended to take part in the formation of hydrides with reagent 2 and the bodies contained in sample 1. Means of acid supply 3 comprise a peristaltic pump 15 acting on a tube 14 which leads into drain 30 via a needle 32.

Drain 30, detailed in FIG. 2, has a diameter D1 of 1 cm for example. Its lower part is plugged up by a stopper 34 through which crosses evacuation capillary 33. Capillary 33 extends over into drain 30 over a height H and diameter D2. The values of H and D2 are for example 1 mm. Evacuation capillary 33 therefore forms in drain 30 a mixing area 35 approximately round cylindrical having a diameter D1 and a height H. With the chosen numerical values, this mixing zone 35 has a volume in the region of 100 μl Before each series of measurements sample 1 to be analysed is placed in solution form upstream of supply means 10, 11 of nebuliser 20. Sample 1 comprises one or more bodies to be determined, preferably including at least one element likely to form hydrides. Such element may, for example, be a heavy metal such as bismuth, germanium, mercury or tin, a metalloid such as arsenic, selenium or tellurium, or a semimetal such as antimony. As several of these elements are toxic, their measurement with a very low detection limit is essential in particular in water. It is known that these elements are able to form volatile hydrides when placed in the presence of one or more appropriate reagents and acids.

By way of illustration, the chemical equation is represented below giving the formation of a hydride using an element E. This element E is chosen from among As, Bi, Ge, Sb, Se, Sn and Te. Reagent 2 is sodium borohydride, $NaBH_4$, and acid 3 is hydrochloric acid HCl.

$$NaBH_4 + 3H_2 + HCl \longrightarrow H_3BO_3 + NaCl + 8H$$

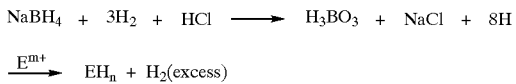

$$\xrightarrow{E^{m+}} EH_n + H_2(excess)$$

In this equation, m may be or may not be equal to n. The reactive and acid elements given by way of example are not limitative, any other choice being possible provided that the elements may be reduced to volatile hydrides. Those skilled in the art know the possible reactions which may be used with the system and method of nebulisation of the invention.

Chosen reagent 2 and acid 3 are respectively placed upstream of supply means 12, 13, 31 and 14, 15, 32. The concentrations of sample 1, reagent 2 and acid 3 are advantageously optimised in such manner as to reduce the detection limit without deteriorating operating conditions.

In operation, sample 1 in liquid form and vector gas 4, argon for example, are introduced into nebuliser 20, and sample 1 is sprayed into droplets 5 in suspension in the gas. The pressure in Scott chamber 27 is maintained constant and the feed flow of sample 1 and supply of vector gas 4 are continuous and constant. The first part of droplets 5a is led directly to plasma torch 40 and subjected to ICP-AES while the second part of droplets 5b arrives in liquid form in mixing area 35.

Reagent 2 and acid 3 are introduced into drain 30 at continuous, constant flow rates. They mix with the bodies contained in sample 1 and are led to mixing area 35, thereby producing a gas 6 formed of volatile hydrides. This gas rises as far as aerosol outlet 29, mixing with the first part of droplets 5a to form an aerosol 7 subjected to ICP-AES. The level of liquid in mixing area 35 is maintained constant, level with the evacuation capillary 33 using pumping means 16, 17, 33 which evacuate residual liquid 8 at a continuous, constant evacuation rate.

The low volume of reaction restricts the formation of hydrogen, and prevents disturbances in plasma torch 40. It is also very important to maintain the level constant in mixing area 35 to ensure measurement stability.

As an illustration, a judicious choice is given below of numerical values in a particular example of embodiment. As the object of spectroscopic analysis is to determine in particular at least one of the above-mentioned elements for chemical reaction, reagent 2 is sodium borohydride and acid 3 is hydrochloric acid. Concentrations of reagent 2 and acid 3 are respectively in the region of 1% $NaBH_4$ in 0.5 M and 6 M NaOH, their introduction rates being in the region of 1 ml/min. The evacuation rate of the residual liquid is higher than 3 ml/min, and that of the supply of gas vector 4 lies between 0.3 l/min and 0.5 l/min. The pressure of vector gas 4 entering nebuliser 20 is in the region of 3 bars.

In the system of the invention, the bodies likely to react in sample 1, reagent 2 and acid 3 mix together in a much reduced area. This situation is highly favourable for measurement stability and also permits rapid evacuation from mixing area 35 so that it is easy to change from one sample to another.

Since the proportion of sample 1 entering the first part of droplets 5a is between 1.5 and 2%, nearly 98 to 98.5% of sample 1 is transferred via the second part of droplets 5b towards drain 30. The generation of hydrides from the elements concerned at this point is therefore effective for almost all of sample 1 which reaches mixing area 35. With emission spectrometry it is therefore possible to determine with great precision the elements which formed hydrides in mixing area 35. This determination completes that obtained for other elements contained in the first part of droplets 5a, such as for example calcium, copper or magnesium.

As an example, with further reference to the above illustration, but with nitric acid instead of hydrochloric acid, and focusing on the element mercury, the detection limit may reach 40 PPT (Parts Per Trillion) for an error of 3 σ whereas it reaches 2000 PPT in the absence of hydride generation in drain 30.

Supply means 12, 13, 14, 15, 31, 32 of drain 30 may be completed when it is suitable or necessary to introduce other products in mixing area 35. An additional needle, for example, may be added to existing needles 31, 32 to supply, for example, drain 30 with two acids simultaneously. This layout may in particular be appropriate for lead, the first of such two needles being intended for hydrochloric acid and the second for sulphuric acid.

Continuous, constant flow rates both for the introduction of products and for pumping of drain 30 are particularly suitable for the system of the invention. However, it is possible to make one or more of these flow rates to vary while remaining within the limits of the invention. Also the supply rate of vector gas 4 may itself be modified during the course of time. Batch processing may also be considered, but the generation of hydrides makes preferable a continuous reaction obtained through continuous, constant flows for reasons of stability.

The separate introduction of sample 1 and acid 3 with a view to hydride generation is an optional aspect of the invention of particular interest. It is however possible to carry out beforehand the mixture of sample and acid and to nebulise the composition obtained with nebuliser 20. This mixing upstream of the acid and sample is less advantageous than the described preferred embodiment as the coexistence of the acid and sample in sprayed droplets 5 is likely to cause disturbances.

Drain 30 may have a form other than the round, cylindrical form given in the example of embodiment. It may, for example, be conical, comprise a polygonal section such as rectangular or hexahedral, or even an elliptic section.

A variant of the embodiment of the system of the invention comprises a chamber placed downstream from nebuliser 20 opening onto Scott chamber 27. This chamber may have any form, such as one of those mentioned for drain 30 in the main embodiment, and is advantageously round cylindrical. It is supplied with sample 1 through independent supply means or via diversion of supply means 10, 11 of nebuliser 20. Supply means 12, 13, 31 of reagent 2 and possibly those 14, 15, 32 of acid 3 are then no longer placed on drain 30 as in the previous embodiment of the invention, but on this chamber. Also, pumping means allow a constant level of liquid to be maintained therein. In this alternative embodiment the chamber opening onto Scott chamber 27 therefore acts as hydride generator, in the same manner as drain 30 in the main embodiment.

Any other type of pneumatic nebuliser, other than the concentric flow nebuliser in the example of embodiment, may be used such as a cross flow nebuliser or a Babington nebuliser.

Also, Scott chamber 27 may be replaced by any other spray chamber such as a cyclone chamber.

Although a pneumatic nebuliser is particularly simple and cheap to set up, it may also be replaced by other spray means, such as an ultrasound nebuliser. In this case, the means of body separation usually comprises a spray chamber at the exit of the nebuliser and a separation chamber connected to the first by a duct, comprising a drain and an aerosol outlet directed towards the spectrometry means. The hydride generator then preferably opens onto the separation chamber.

The system may comprise several nebulisers and several hydride generators. This second possibility is for example implemented by placing several chambers opening onto the spray chamber, of at least one is placed downstream from the nebuliser and acts as hydride generator as described previously.

The system of the invention may be used for any form of analytical atomic spectrometry, through emission, absorption, fluorescence, or mass spectrometry.

I claim:

1. A system for introducing a liquid sample (1) containing at least one element to be analyzed by analytical atomic spectrometry, comprising:

at least one nebulizer (20) for spraying the liquid sample (1) into fine droplets (5), said at least one nebulizer having at least one liquid inlet (21) intended to receive the liquid sample (1), at least one gas inlet (22) intended to receive a vector gas (4) and at least one outlet (23) intended to expel the droplets (5) in suspension in the vector gas (4), liquid sample supply means (10, 11) for supplying said at least one nebulizer (20) with the liquid sample (1), connected to said liquid inlet (21) of said at least one nebulizer (20), vector gas supply means (18) for supplying said at least one nebulizer with the vector gas (4), connected to said gas inlet (22) of said at least one nebulizer (20), separation means (27) for separating said droplets (5) into a first part (5a) in aerosol form and a second part (5b) in liquid form, said separation means (27) is placed at said outlet (23) of said at least one nebulizer (20), said separation means (27) comprising at least one aerosol outlet (29) intended to expel said first part (5a) of the droplets to be analyzed in aerosol form towards means of analytical atomic spectrometry (40), at least one drain (30) intended to evacuate residual liquid (8), said drain (30) receiving said second part (5b) of the droplets to be analysed in liquid form and serving to generate at least one hydride (6) produced from said at least one element in said second part (5b) and carried by the vector gas (4), reagent supply means (12, 13, 31) for supplying said drain (30) with at least one reagent (2) intended to react with said at least one element in said drain (30) to form said at least one hydride (6), characterised in that said drain (30) is plugged up and is fitted with evacuation means (16, 17, 33) for controlled evacuation of said residual liquid (8) contained in said drain.

2. A sample introduction system in accordance with claim 1, characterized in that said means of separation (27) comprises a spray chamber.

3. A sample introduction system in accordance with claim 2, further comprising: acid supply means (14, 15, 32) supplying said at least one drain (30) with acid (3).

4. A sample introduction system in accordance with claim 1, further comprising acid supply means (14, 15, 32), the sample introduction system characterized in that said sample supply means (10, 11), said reagent supply means (12, 31, 31) and said acid supply means (14, 15, 32) are able to ensure continuous, constant flows during analysis of said sample.

5. A sample introduction system in accordance to claim 1, characterized in that said at least one nebulizer (20) is a pneumatic nebulizer.

6. A method of introducing a liquid sample (1) containing at least one element to be analysed by analytical atomic spectrometry, in which:

a liquid sample (1) and a vector gas (4) are introduced into a nebulizer (20), said liquid sample (1) is sprayed into fine droplets (5) by said nebulizer (20) and said droplets (5) suspended in the vector gas are led into means of separating (27) said droplets into a first part (5a) in aerosol form and a second part (5b) in liquid form, the first part (5a) of said droplets to be analysed is expelled in aerosol form towards analytical atomic spectrometry means (40), said at least one element (5a) contained in the aerosol is analysed by analytical atomic spectrometry, and in which:

the second part (5b) said droplets to be analysed is received in liquid form in a drain (30), at least one reagent (2) is introduced into said drain (30) and reacted with said at least one element (5b) to form at least one hydride (6), said at least one hydride (6) is generated in said drain (30) and said at least one hydride (6) is carried by the vector gas (4) toward the spectrometry means (40), and residual liquid (8) is evacuated through said drain (30), characterised in that said residual liquid (8) is evacuated under conditions of constricted and controlled flow from said drain (30) by evacuation means (16, 17, 33).

7. A method in accordance with claim 6, characterised in that said liquid sample (1) in said nebuliser (20) and said at least one reagent (2) in said hydride generating drain (30) are introduced at continuous and constant flow rates during analysis.

8. A method in accordance with claim 7, characterised in that a level (H) of liquid (35) is maintained constant in said drain (30).

9. Method in accordance with claim 8, characterised in that said at least one element to be analysed is As, Bi, Ge, Hg, Pb, Sb, Se, Sn or Te.

10. A sample introduction system in accordance with claim 2, characterized in that said sample supply means (10, 11) and said reagent supply means (12, 13, 31) are able to ensure continuous, constant flows during analysis of said sample.

11. A sample introduction system in accordance with claim 3, characterized in that said sample supply means (10, 11) and said reagent supply means (12, 13, 31), and said acid supply means (14, 15, 32) are able to ensure continuous, constant flows during analysis of said sample.

12. A sample introduction system in accordance with claim 2, characterized in that said at least one nebulizer (20) is a pneumatic nebulizer.

13. A sample introduction system in accordance with claim 3, characterized in that said at least one nebulizer (20) is a pneumatic nebulizer.

14. A sample introduction system in accordance with claim 4, characterized in that said at least one nebulizer (20) is a pneumatic nebulizer.

15. A sample introduction system in accordance with claim 10, characterized in that said at least one nebulizer (20) is a pneumatic nebulizer.

16. A sample introduction system in accordance with claim 11, characterized in that said at least one nebulizer (20) is a pneumatic nebulizer.

17. A method in accordance with claim 6, further characterized by: supplying said drain with acid via acid supply means.

18. A method in accordance with claim 17, characterized in that said liquid sample in said nebulizer, said at least one reagent, and said acid in said hydride generating drain are introduced at continuous and constant flow rates during analysis.

19. A method in accordance with claim 18, characterized in that a level (H) of liquid (35) is maintained constant in said drain (30).

20. Method in accordance with claim 19, characterised in that said at least one element to be analysed is As, Bi, Ge, Hg, Pb, Sb, Se, Sn or Te.

21. A sample introduction system in accordance with claim 1, wherein said evacuation means of the drain (30) comprises a capillary having a diameter (D2) and extending into the drain at a height (H) so as to maintain a constant liquid level of said height (H) in said drain (30).

22. A sample introduction system in accordance with claim 21, wherein said diameter of said capillary is substantially equal to said height (H); and, wherein said drain (30) has a diameter (D1) that is larger than the diameter (D2) of said capillary by a factor of ten.

23. A method in accordance with claim 6, wherein said evacuation means of the drain (30) comprises a capillary having a diameter (D2) and extending into the drain at a height (H) so as to maintain a constant liquid level of said height (H) in said drain (30).

24. A method in accordance with claim 23, wherein said diameter of said capillary is substantially equal to said height (H); and, wherein said drain (30) has a diameter (D1) that is larger than the diameter (D2) of said capillary by a factor of ten.

* * * * *